United States Patent [19]

Ida

[11] 4,421,411
[45] Dec. 20, 1983

[54] PHOTOMETRIC ANALYZER
[75] Inventor: Edward S. Ida, Newark, Del.
[73] Assignee: E. I. Du Pont de Nemours & Co., Wilmington, Del.
[21] Appl. No.: 261,483
[22] Filed: May 7, 1981
[51] Int. Cl.³ .......................... G01J 3/48; G01D 5/36
[52] U.S. Cl. ................................. 356/418; 250/233; 250/339
[58] Field of Search ............... 356/405, 406, 418, 419; 250/434, 351, 343, 339; 350/233, 274

[56] References Cited
U.S. PATENT DOCUMENTS 3,459,951  8/1969  Howarth et al. ................... 250/226
3,526,448  9/1970  Senseny .............................. 350/272
3,955,096  5/1976  Faulhaber .......................... 250/565
4,076,424  2/1978  Ida ..................................... 356/418
4,120,592  10/1978  Fleming et al. ................... 356/201
4,281,897  8/1981  Fletcher ............................. 356/434

Primary Examiner—Vincent P. McGraw
Assistant Examiner—L. A. Dietert

[57]  ABSTRACT

A spectral photometer including a filter wheel driven by a synchronous motor and an analysis circuit. Interference effects of the power line on the output of the photometer are cancelled by provision of a speed changer to achieve each revolution of the filter wheel in the time required for a set, odd number of power line half-cycles to the motor.

4 Claims, 6 Drawing Figures

PHOTOMETRIC ANALYZER

BACKGROUND

This invention relates generally to photometric analyzers and, more particularly, to the analysis of fluid samples according to their absorption spectra.

It is known in the art that the presence or absence and concentration of a constituent can be determined by exposing a fluid sample alternately to reference and analytical beams, detecting the levels of absorption and computing ratios based on the difference in those levels. The wavelength of the analytical beam is preferentially absorbed by the constituent to be analyzed. The wavelength of the reference beam is not absorbed by the constituent to be analyzed but is absorbed by other constituents in substantially the same proportion as the analytical beam. It is also known that two or more constituents can be analyzed with one photometer by placing a rotating filter wheel between a radiation source and a photodetector. The wheel is opaque except for a plurality of reference and analytical filters and is driven by a synchronous motor. Circuitry is provided for receiving the detected signals and generating outputs related to the differences in absorption by different pairs of filters. Frequently, inaccuracies and inconsistencies related to interferences induced from the power line are noted in the recorded results.

SUMMARY

The above and other disadvantages have been overcome in a spectral photometer that has both a filter wheel driven by a synchronous motor and a photodetector in the optical path of light filtered by the wheel. According to the present invention, speed changing means is provided between the motor and filter wheel for reversing the polarity of power line interference at the photodetector on successive revolutions of the wheel. Put differently, the filter wheel is rotated one revolution in the time required for an odd number of power half-cycles to the synchronous motor.

DRAWINGS

DESCRIPTION

Figure 1:
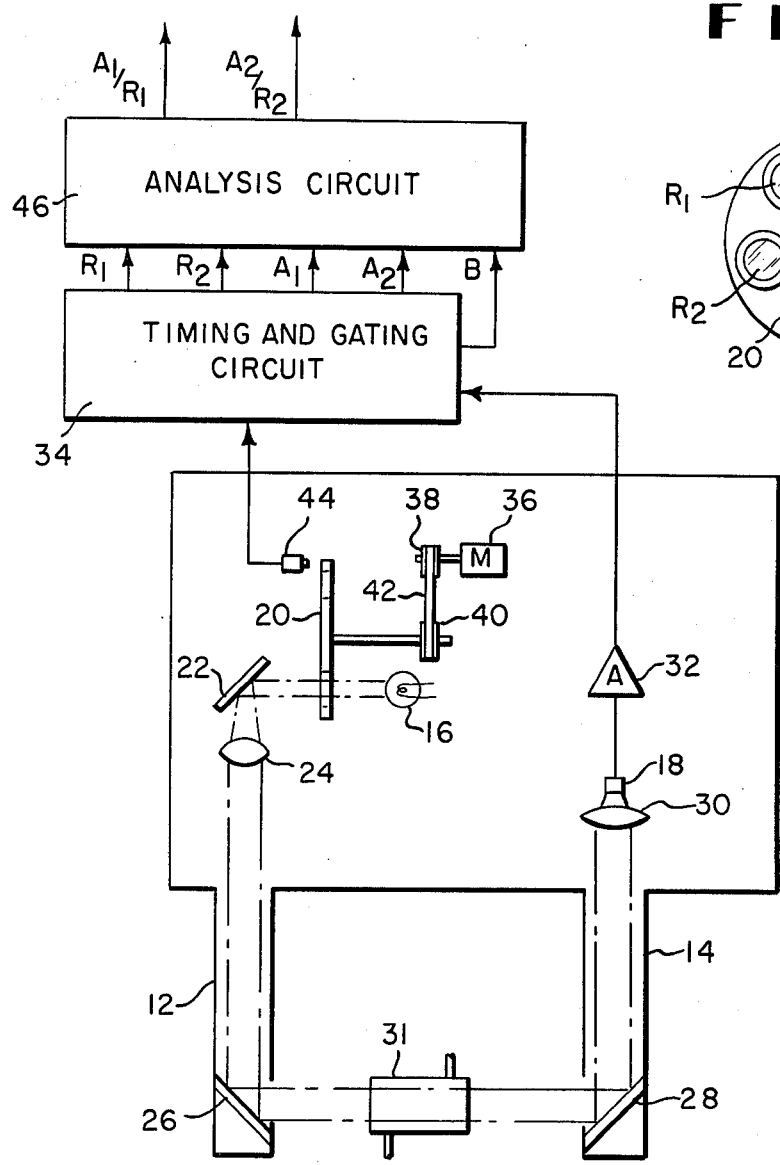
FIG. 1 is a schematic of a spectral photometer incorporating the improvement of the present invention and includes a block diagram of associated circuitry.

In FIG. 1, elements of a spectral photometer are enclosed by a radiation-tight housing 10 that includes conduits 12, 14, through which radiation from a source 16 passes to an infrared (IR) detector 18. Typically, source 16 is a tungsten filament lamp. Elements in the optical path of radiation from source 16 include a filter in a rotating wheel or chopper 20, mirror 22, collimating lens 24, mirrors 26, 28, focusing lens 30 and IR detector 18. Between mirrors 26, 28, there is a cell 31 having transparent windows between which a fluid sample flows. Detector 18 is connected to a preamplifier 32 which, in turn, is connected to a timing and gating circuit 34.

Filter wheel 20 is driven by a 4-pole, hysteresis, synchronous motor 36 having a typical shaft speed of 1800 revolutions per minute (rpm). Instead of a direct drive, the motor shaft is connected to wheel 20 through pulleys 38, 40 and a toothed belt 42. In the illustrated embodiment, the sizes of pulleys 38, 40 are such as to provide a step-down ratio of 5:4 or 1.25, producing a wheel speed of 1440 rpm. Adjacent the periphery of wheel 20, there is an electromagnetic pickup 44 which transmits a timing pulse to circuit 34 for each revolution of the wheel.

Figure 2:
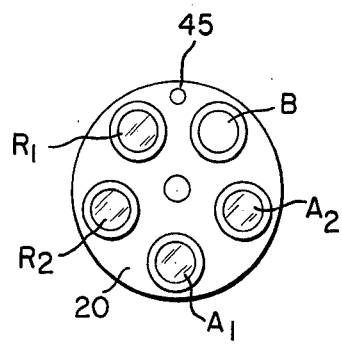
FIG. 2 is a plan view of a filter wheel that is useful in the photometer of FIG. 1.

As shown in FIG. 2, wheel 20 carries five equispaced discs. Four of the discs are interference filters, two for analytical signals ($A_1$ and $A_2$) and two for reference signals ($R_1$ and $R_2$). The fifth, background disc B is an opaque blank. At its periphery, wheel 20 also carries a magnetized insert 45 that is sensed by pickup 44 during each revolution of the wheel. Signals generated by photodetector 18 (FIG. 1) as the discs pass source 16 are applied to an analysis circuit 46 in a gated sequence initiated by each triggering pulse transmitted to timing, gating circuit 34 from pickup 44. Circuits 34, 46 function in the same manner as corresponding circuits disclosed by Ida in U.S. Pat. No. 4,076,424. More particularly, in circuit 46, signals related to the ratios of A/R are generated and applied to a recorder such as a strip chart. The plot of each signal records the presence or absence and concentration of a particular constituent in the sample, for example, the numbers of amine ends and bright polymer solids in a spinning solution of a spandex polymer.

Figure 3:
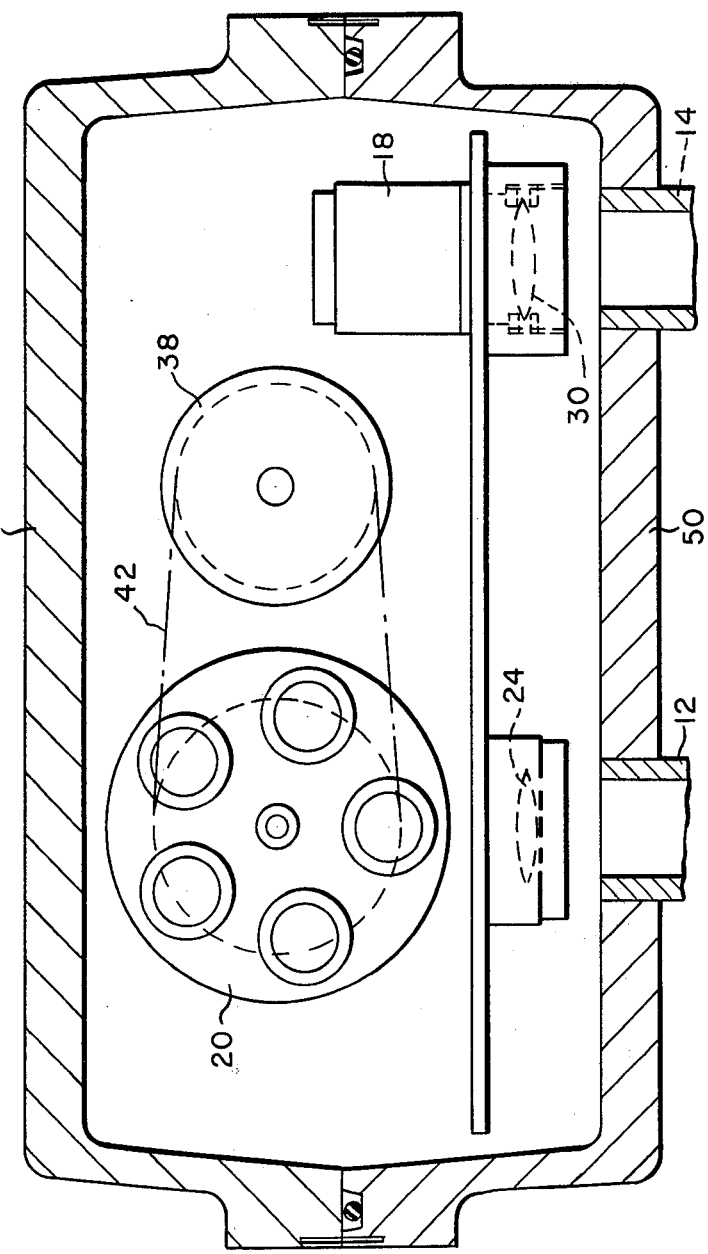
FIGS. 3-5 are side, top and front views, respectively, showing various parts, components and arrangements in an operable embodiment.
Figure 4:
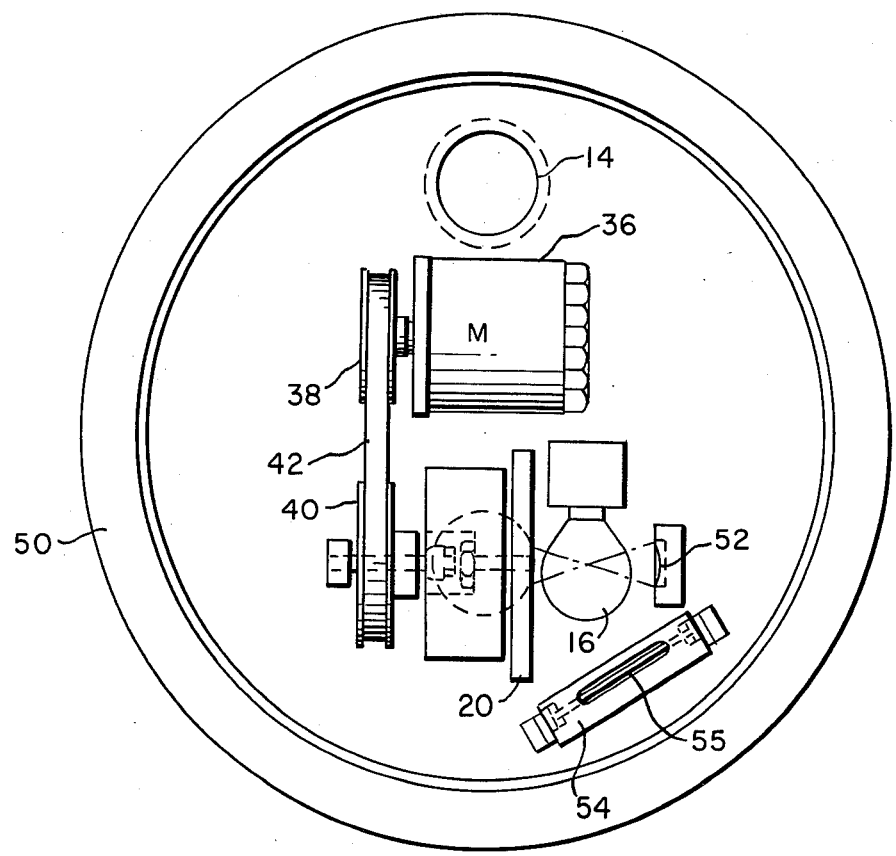
Figure 5:
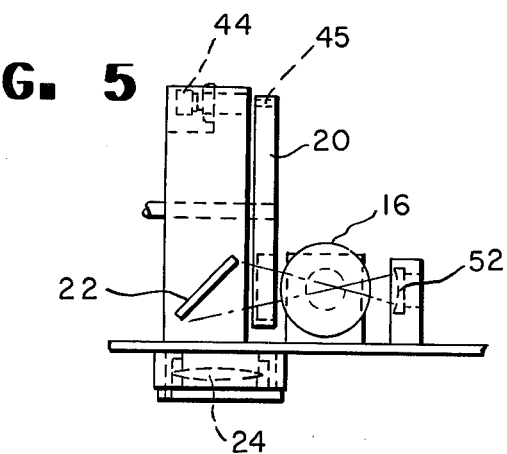

Structural arrangements and relationships between various parts and components are shown in FIGS. 3-5. Housing 10 has upper and lower sections 48, 50. Motor 36 is mounted in section 50 and coupled to wheel 20 through pulleys 38, 40 and belt 42. Lamp 16 is located between wheel 20 and a spherical reflector 52. IR light passes through the discs in wheel 20 and is reflected by mirror 22 through lens 24 to conduit 12. After passing through the sample in cell 31 (FIG. 1), the light pulses reenter housing 10 through conduit 14 and are focused on photodetector 18 by lens 30. Amplifier 32 (FIG. 1) is located in a housing 54 on a printed circuit board 55.

Figure 6:
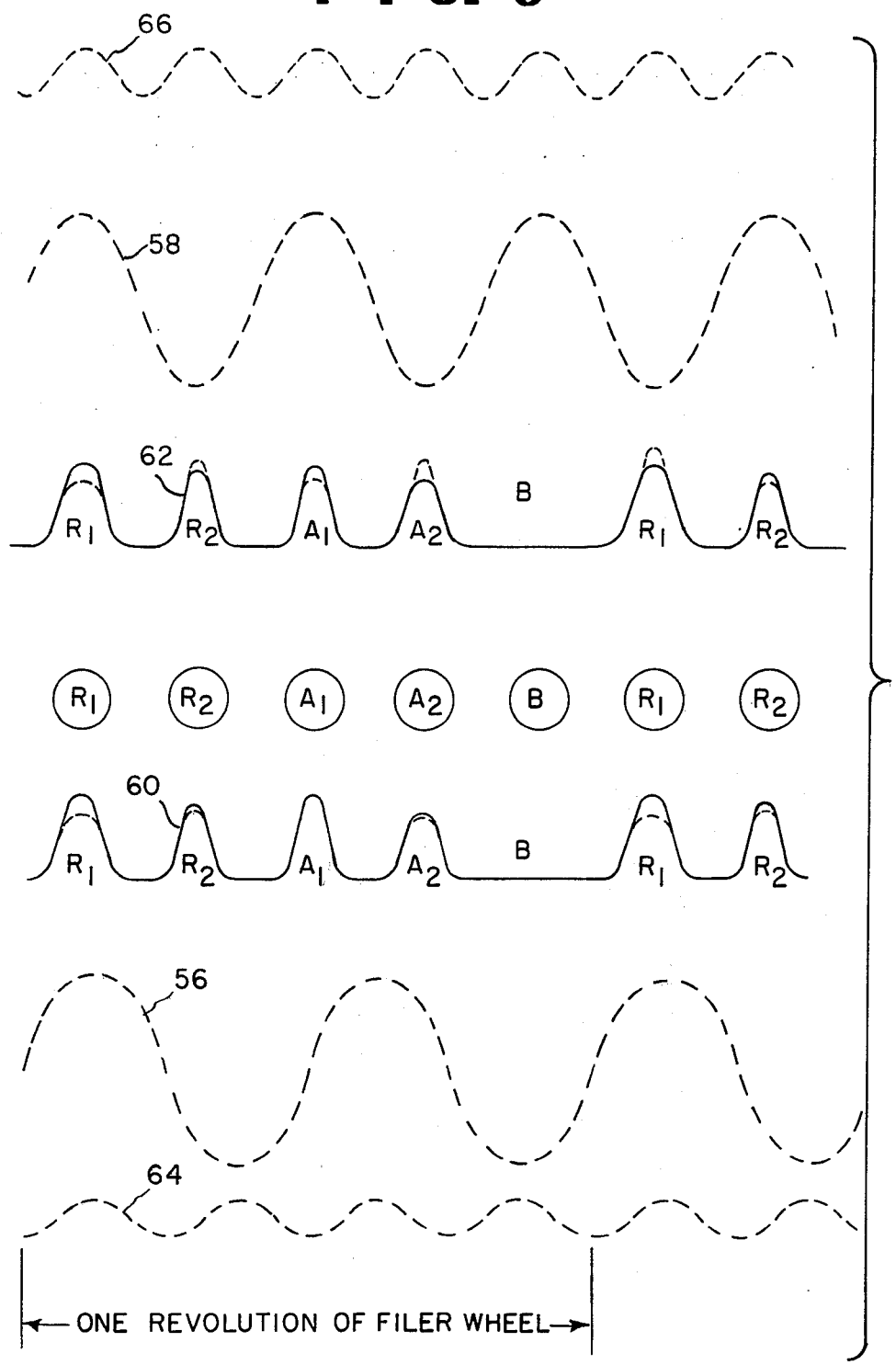
FIG. 6 is a schematic illustration of relationships between filter locations and power line effects.

It has been noted above that a hysteresis, synchronous motor having a shaft speed of 1800 rpm is usually used in photometers of the type disclosed herein. Polarized, synchronous motors have also been used. In either event, with a direct drive of filter wheel 20, two full cycles of line power are required for each revolution of wheel 20, as shown in FIG. 6 by a waveform 56. With a step-down ratio of 1.25, there are five half-cycles of line power for each revolution of wheel 20, as shown by a waveform 58. Exemplary analog signal pulses from amplifier 32 (FIG. 1) are shown at 60, 62 in FIG. 6 for purposes of comparison with waveforms 56, 58, respectively.

Power line interference pickup is radiated electromagnetic noise that has the power line frequency as its principal component. Due to its vectorial nature, i.e., having both phase and amplitude, it is additive to the signal appearing at the input terminal of preamplifier 32, thus introducing either an additive or subtractive, spurious, sinusoidal variation in the actual output of the preamplifier. Exemplary actual responses are shown by broken line peaks and true responses by solid line peaks in analog pulse trains 60, 62. It is apparent on inspection that the spurious signals cause pulse train 60 to vary in amplitude from pulse to pulse and the effects are taken in the same direction in successive revolutions of wheel 20. Thus, ratios computed from pulse train 60 would be both inaccurate and inconsistent. By comparison, the effect of the spurious signals in the pulses in train 62 is similar; but the respective direction alternates in successive revolutions of wheel 20. Thus, the spurious signals are cancelled or nulled before the signals are averaged in circuit 46; as a consequence, accurate and consistent ratios are computed.

If a polarized, synchronous motor were to be used, the phase of pickup from the power line is not affected at restart. However, when hysteresis, synchronous motor 36 is stopped and restarted, as by a power interruption, it does not lock reliably into the same angular relationship of the filters relative to the phase of the power line. On inspection of FIG. 6, it is apparent that any lead or lag of the filter discs with respect to the phase of line power introduces additional inconsistencies in at least the amplitudes of the spurious signals. With pulse train 60, this is an additional and unpredictable source of inaccuracies in the computed ratios. On the other hand, as noted above, the spurious signals in pulse train 62 would still be nulled as the signals are averaged in circuit 46.

The step-down ratio discussed above, namely, 5:4 or 1.25, allows adequate time for response by circuits 34, 46 when the interference filters have peak transmission wavelengths of about 1000–2000 nanometers (nm). For longer wavelengths, which involve longer detector response times, or for wheels with more filters, higher ratios are appropriate, for example, 1.75 or 2.25. Similarly, for shorter wavelengths or for wheels with fewer filters, a lower ratio is appropriate, for example, 0.75. The controlling factor is that radiated power line noise pickup be cancelled by rotating the filter wheel once per each prescribed odd integral multiple of power half-cycles. With such an odd number of power half-cycles, successive revolutions of the filter wheel produce polarity reversals of any sensed power line frequency interference pickup in the electronics or the detector itself. Thus, by averaging these polarity reversals, before computing any ratios, the pickup interference is effectively cancelled. That effect has been achieved by incorporation of speed changer 38, 40, 42 and by selection of pulley sizes to establish the appropriate, fractional ratio between an odd number of power line half-cycles for each revolution of filter wheel 20 and the even number of power half-cycles for each revolution of motor 36. More specifically, the ratio of motor speed, m, to filter wheel speed, f, is:

$$m/f = N/k$$

where N is an odd number of power half-cycles per revolution of the filter wheel and k is the even number of power half-cycles per revolution of the motor shaft.

As distinguished from power line interference, thermal ripple is a disturbance in lamp intensity that occurs at twice the power line frequency. Its origin is the occurrence of zero crossings in the AC power supply which cause a small flicker in the radiated intensity of source 16. Waveforms of thermal ripple corresponding to waveforms 56, 58 are shown at 64, 66, respectively. A comparison of pulse train 60 with waveform 64 shows that thermal ripple affects the pulses in train 60 differently when wheel 20 is driven directly. A comparison of pulse train 62 with waveform 66 shows that the pulses are affected proportionally when the discs on wheel 20 are spaced radially by angular displacements corresponding to an integral number of power half-cycles. In the illustrated embodiment, there are five discs and five half-cycles of line power per revolution of filter wheel 20.

Once the constituents to be analyzed have been identified, appropriate filter discs and drive pulleys are selected and installed. If the analysis is to be continuous, a flow cell of the type described above is positioned between mirrors 26, 28 and connected to a source of the fluid. If, instead, spot analyses are to be made, suitable sampling cells can be loaded, brought to the location of the photometer and positioned, in turn, between the mirrors 26, 28.

What is claimed as new and desired to be secured by Letters Patent is:

1. In a spectral photometer including a filter wheel driven by a synchronous motor, the improvement comprising speed changing means between the motor and filter wheel for rotating the filter wheel one revolution in the time required for an odd number of power half-cycles to the motor.

2. The photometer of claim 1 wherein the filter wheel contains a plurality of angularly spaced, optical filters with the angular separation between adjacent filters corresponding to an integral number of power half-cycles to the motor.

3. The spectral photometer of claim 1 wherein said speed changing means establishes a fractional ratio of motor speed, m, to wheel speed, f, and the ratio is $$m/f = N/k$$

where N is the odd number of power half-cycles per revolution of the wheel and k is the even number of power half-cycles per revolution of the motor.

4. In a spectral photometer including a filter wheel driven by a synchronous motor and a photodetector in the optical path of light filtered by the wheel, the improvement comprising speed changing means between the motor and filter wheel for reversing the polarity of power line interference at the photodetector on successive revolutions of the wheel.

* * * * *